United States Patent [19]
Grichnik

[11] Patent Number: 5,586,162
[45] Date of Patent: Dec. 17, 1996

[54] PORTABLE X-RAY MACHINE

[75] Inventor: James Grichnik, Phelps, Wis.

[73] Assignee: Micro Focus Imaging Corp., Wheeling, Ill.

[21] Appl. No.: 263,652

[22] Filed: Jun. 20, 1994

[51] Int. Cl.⁶ .................................................. H05G 1/02
[52] U.S. Cl. ............................................ 378/198; 378/189
[58] Field of Search .................................. 378/194–198, 378/193, 189

[56] References Cited

U.S. PATENT DOCUMENTS

| | | | |
|---|---|---|---|
| 3,702,935 | 11/1972 | Carey et al. | 378/198 |
| 4,326,131 | 4/1982 | Waerve | 378/198 |
| 4,775,994 | 10/1988 | Kranvogel | 378/198 |
| 5,067,145 | 11/1991 | Siczek et al. | 378/198 |

*Primary Examiner*—David P. Porta
*Assistant Examiner*—Don Wong
*Attorney, Agent, or Firm*—Leo J. Aubel

[57] ABSTRACT

A portable X-ray apparatus comprising a cart carrying an X-ray generator unit and an image intensifier unit, both in a stowed transport position. One of said units is mounted on the distal end of a support arm pivotable mounted on the cart, the arm is moveable from a stowed first position to an operative open position to position the unit it is carrying to be in an open spaced alignment, whereby in the operative position on the two units are effectively on respective tips of a C-shaped configuration thereby allowing a patient to be positioned between the units to enable taking an X-ray of the patient.

9 Claims, 6 Drawing Sheets

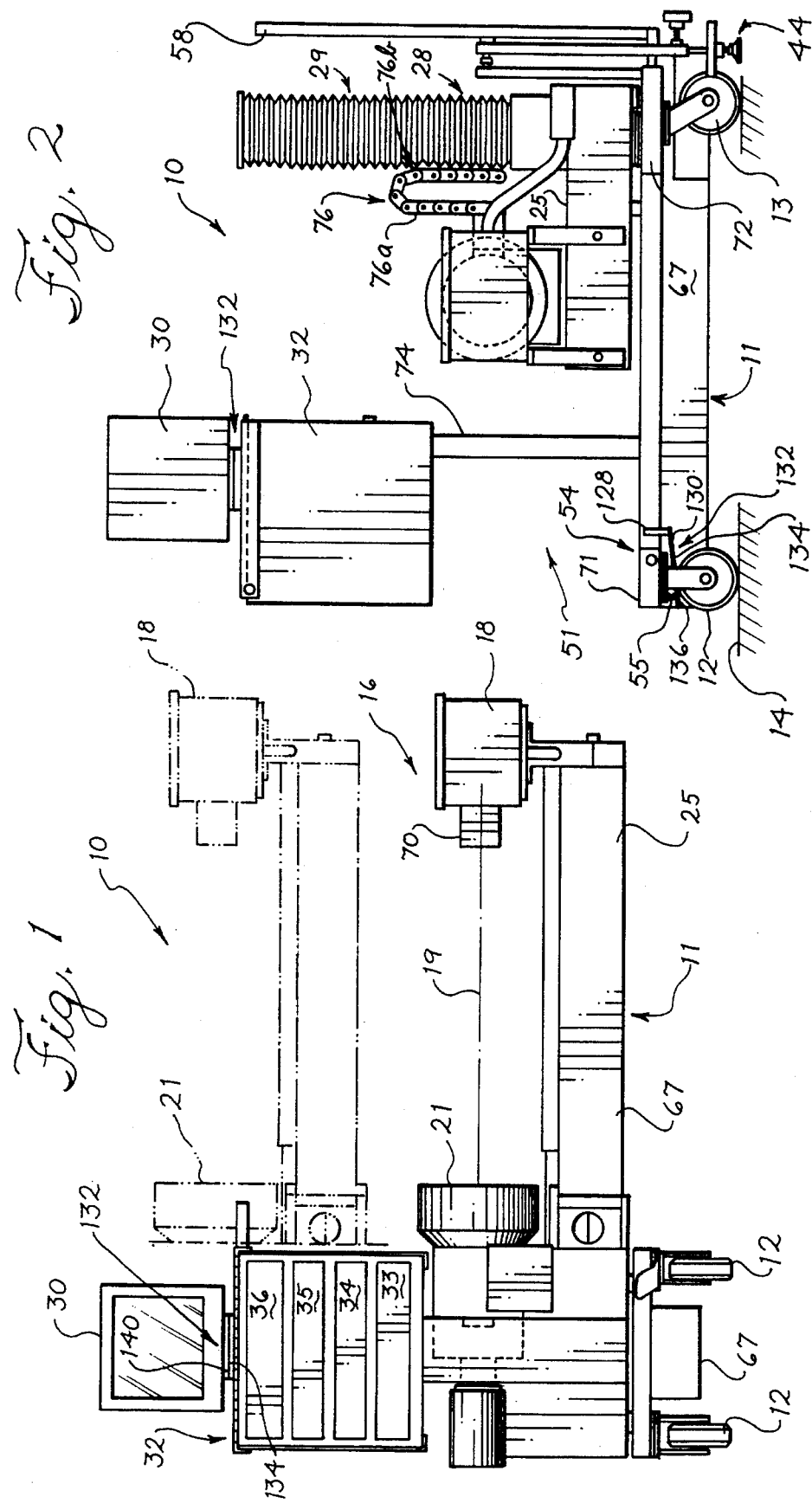

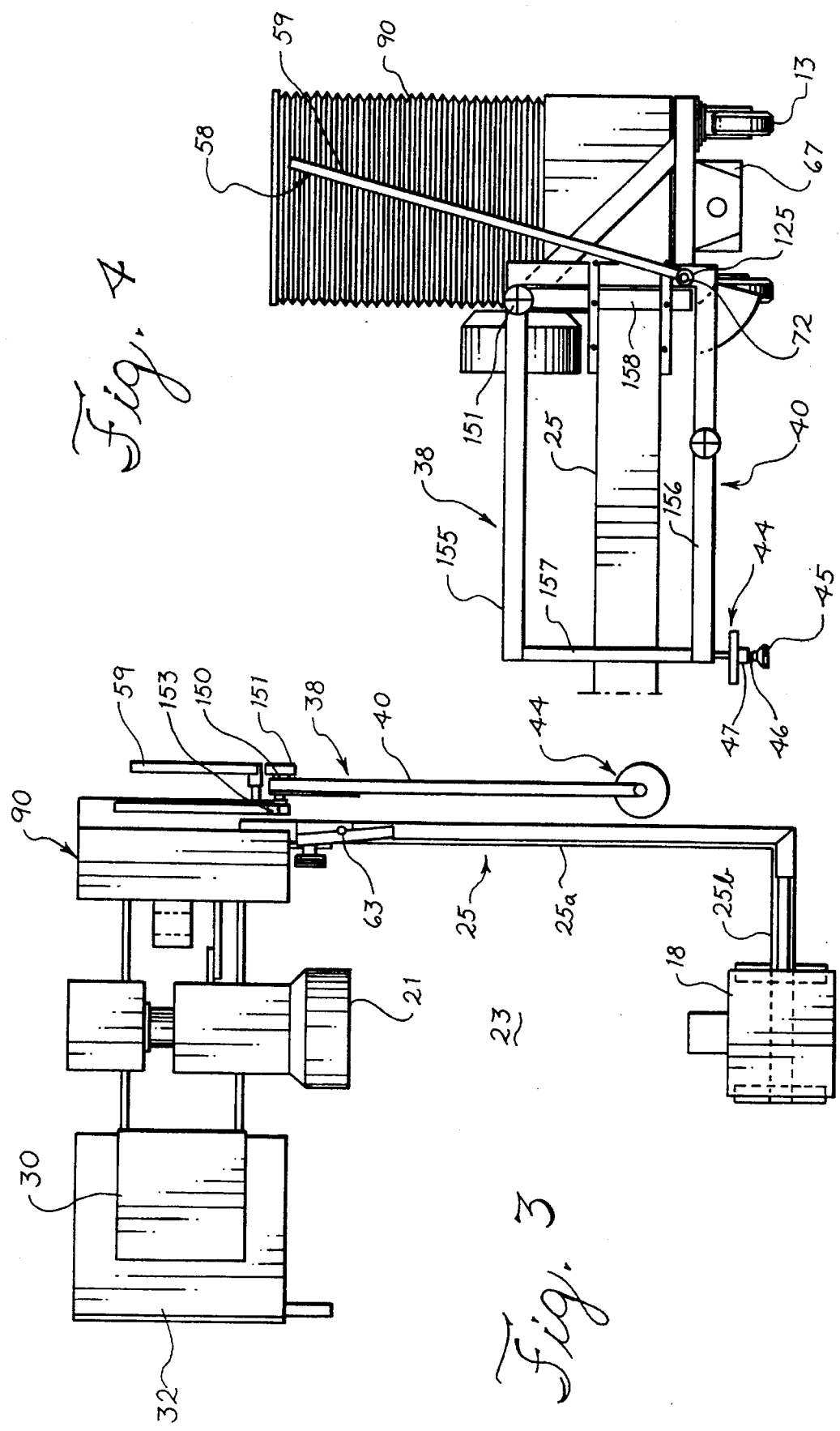

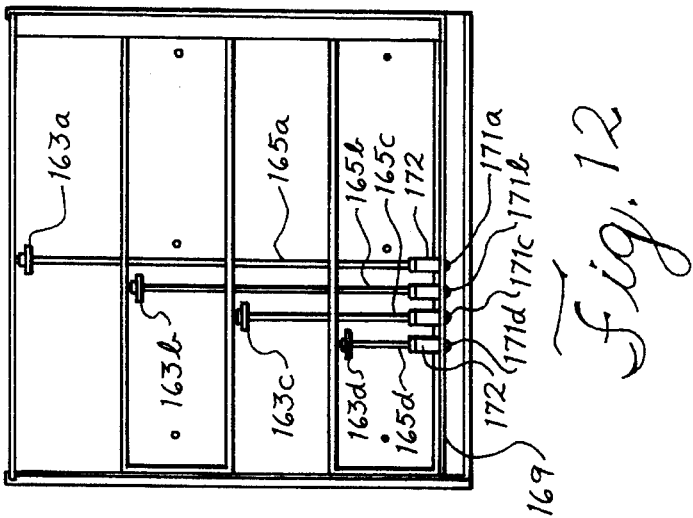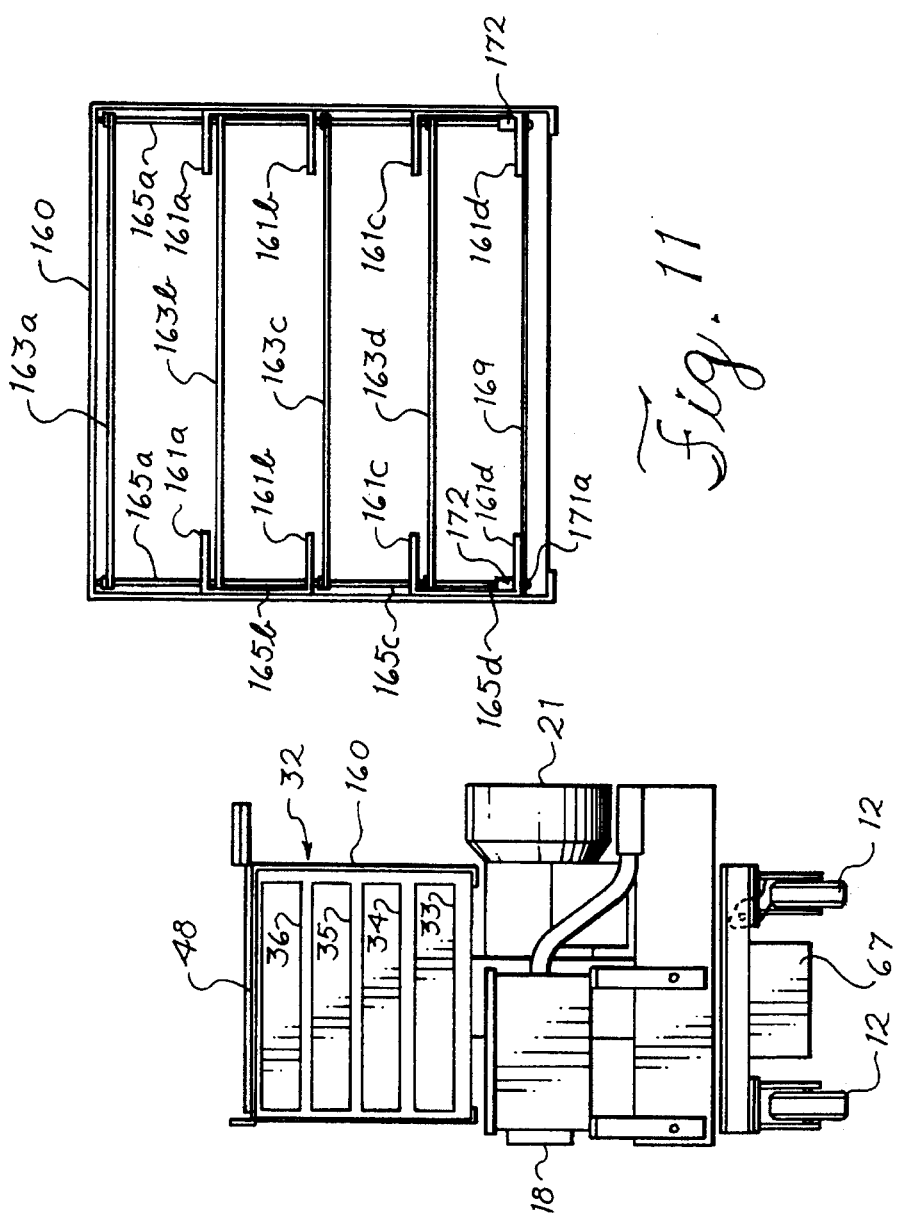

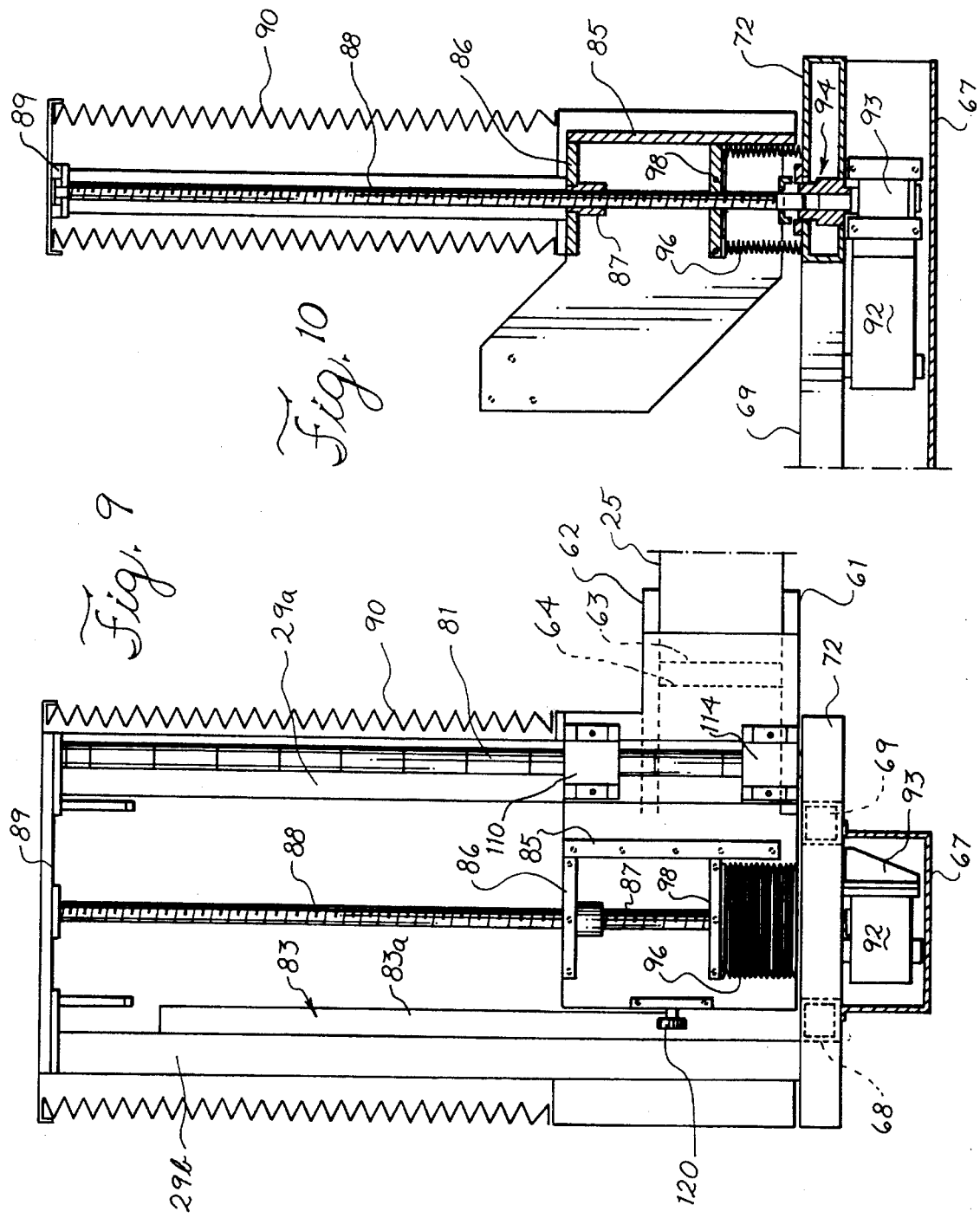

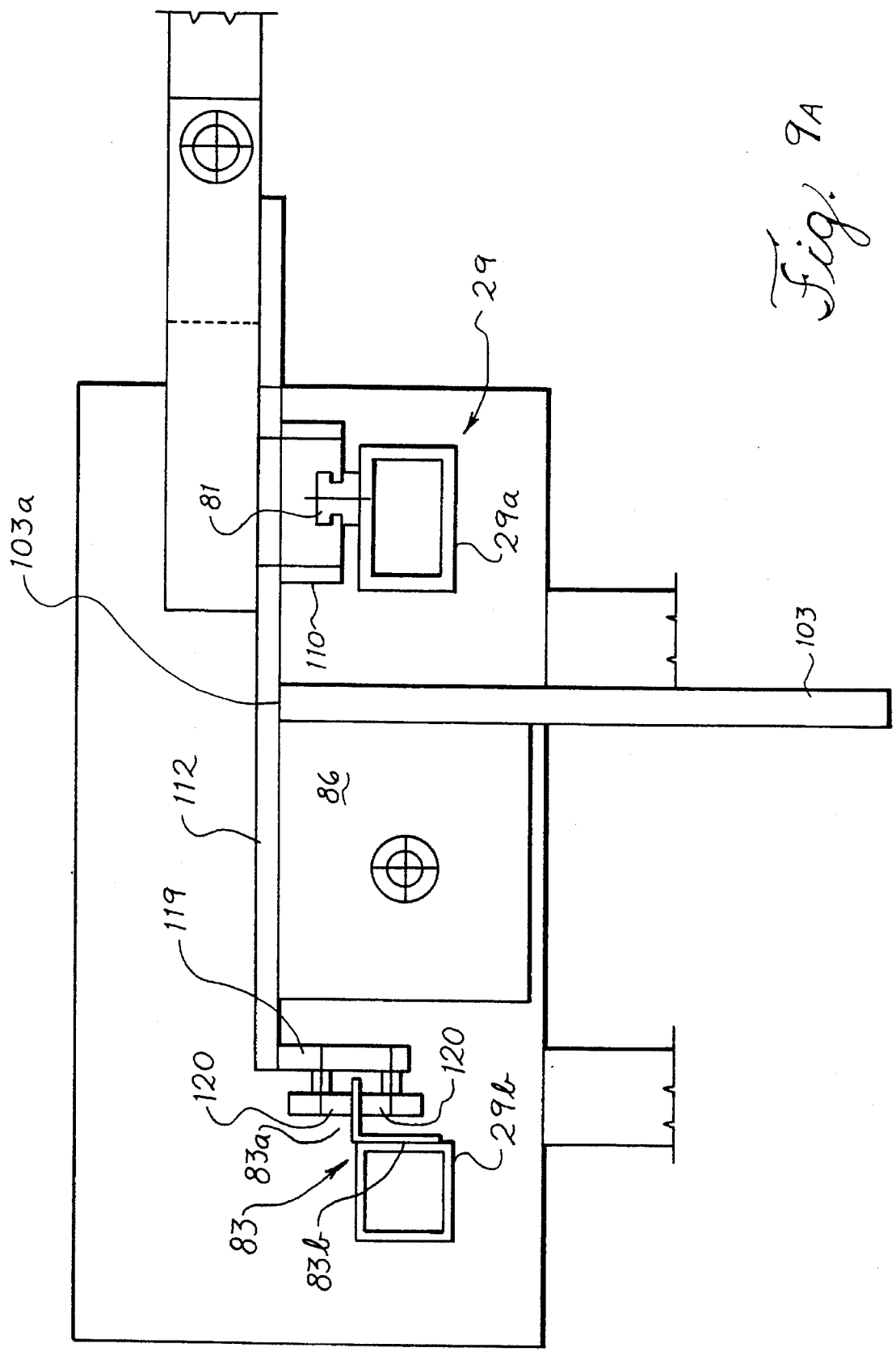

PORTABLE X-RAY MACHINE

BACKGROUND OF THE INVENTION

This invention relates to a portable X-ray apparatus, and more particularly, to a portable X-ray apparatus that can be moved from building to building and transported on a small vehicle such as a van.

The present invention relates to the provision of a portable X-ray apparatus which is on a wheeled cart, which may be rolled into position within a nursing home or other medical facility for the taking of X-rays of a few patients. Typically, the X-ray apparatus will then be wheeled from one nursing home into a truck or a van, or other mode of transport and then transported to another facility, such as a nursing home, where it will be unloaded and taken into a building for use with another set of patients. Often the transport van has a particular size which imposes a severe restraint on the size and the shape of the X-ray apparatus if it is to fit into the van. An additional size constraint is that the X-ray unit should be able to be wheeled through a typical door in an institution, and also put in a conventional elevator. Often the doors are as little as 28" in width and the typical depth in an elevator is about 57". Most vans, without being reconstructed or specially adapted, will take a maximum height of about 40" for the X-ray apparatus. The present invention is not limited to these particular dimensions, but these dimensions do define a particular volume into which the portable X-ray apparatus should be configured in order to be transported in a van, rolled through doorways and fitted into elevators in facilities, such as nursing homes.

The typical X-ray apparatus includes a C-arm which supports an X-ray generator which generates the X-ray beam, which is collimated to pass through the patient to an image intensifier. The generator and image intensifier are generally vertically movable so that they may be positioned at a given height with respect to a particular patient. The patients vary substantially in height and the X-ray unit must be shifted through a fairly wide, vertical adjustment to X-ray these differently sized patients. Usually the C-arm extends out about four feet from the image intensifier; and therefore, it is necessary that the C-arm be foldable or otherwise swung into a stowed or a transport mode and be swung out to a working position or working mode.

Manifestly, the image intensifier and the X-ray generator could be reversed in their positions and the image intensifier could be swung outwardly on a C-arm. In any event, the C-arm, having the X-ray unit thereon, will be extended considerably outward of the cart. This provides a problem with stability. The 70 lb. X-ray generator at the end of a four foot arm must be very stable in order to provide the images desired. That is, the C-arm and the X-ray generator cannot wiggle or otherwise be moved during the X-ray operation. In addition to the X-ray unit, there is usually also a video monitor which allows the operator to view the X-ray images as they are being taken. In the preferred embodiment of the invention, the X-ray unit is an actual fluoroscopic unit in which the X-ray images are moving images showing the person swallowing; and these images are recorded on video tapes by video tape recorders. In addition to the stacking of one or more VCRs on the portable cart, it is also desirable to carry on the cart suitable electronics for image enhancement and also a computer for controlling the operation of the X-ray unit. This preferred and illustrated embodiment of the invention results in a cart which, with the X-ray equipment, VCRs, computer and electronics, weighs as much as 400 lbs.

It can be appreciated that with the 400 lb. portable X-ray apparatus on wheels that it should be braked against running away from the operator as when the cart is going down a ramp, or is being pushed up a ramp. Often the cart must be pushed over soft carpeting as well as over concrete in parking lots,, and of course, moved up and down ramps. It is most desirable that the operation be relatively fail-safe and that brakes be applied automatically so that the cart cannot be a runaway and cause damage to the people or to the cart itself should the operator lose control of the cart.

Further considerations are that the X-ray apparatus ought to be relatively rugged in that it should withstand the abuse encountered in being moved several times a day from one establishment to another establishment. Because of frequent moving from establishment to establishment, the set-up time and take-down time also become important factors. Thus, the portable X-ray apparatus should be relatively quick and easy to set up and take down so that there is not a lot of time-consuming labor involved or other time-consuming acts which would limit the amount of useful time available for taking X-rays during a given work day.

SUMMARY OF THE INVENTION

In accordance with the present invention, there is provided a wheeled X-ray apparatus which includes a wheeled cart on which is mounted a foldable C-arm for carrying an X-ray unit. There is also provided a video monitor which is movable and pivoted inwardly to a stowed position, and which can be swung upwardly to a working position above the height dimension necessary for the transport mode. The preferred X-ray cart apparatus also includes a separate stabilizing arm which swings outwardly into engagement with the floor to provide an outboard support to stabilize the X-ray cart against tipping, to assist in holding the X-ray unit on the C-arm against wiggling, and to maintain alignment with the other X-ray unit, i.e., the image intensifier.

In accordance with another important aspect of the invention, the cart is provided to be auto locking in the sense that if the operator lets go of the cart or takes his hand off the braking actuator, the cart automatically brakes against further movement so that it will not run away. This is particularly important where the cart is being pushed up or down a ramp and has a tendency to want to take off under its own weight when it weighs as much as 450 lbs.

In the preferred form, the X-ray cart has a transport mode or condition in which the pivotally-mounted C-arm which carries the X-ray generator, may be pivoted to move the X-ray generator inwardly into vertical alignment within the cart volume and into vertical alignment with an electronic rack holding video recorders and electronic equipment. The video monitor is also pivoted downwardly to a position over the top of the image intensifier for the transport mode. In the working mode, the video monitor is swung upwardly above the top of the upper height limit. Also, in the preferred embodiment of the invention, the actual height at which the X-ray unit travels is higher than the volume constraint for the particular height limit. The lifting apparatus for the C-arm and the X-ray unit includes a pair of columns, the upper ends of which are encased in a bellows to keep the patient from contact with moving parts.

DETAILED DESCRIPTION OF THE DRAWINGS

The invention will become apparent from the following detailed description when taken into conjunction with the accompanying drawings in which:

FIG. 1 is a front end view of the X-ray apparatus in its working condition and constructed in accordance with the preferred embodiment of the invention;

FIG. 2 is a side, elevational view of the X-ray apparatus of FIG. 1;

FIG. 3 is a plan view of the X-ray apparatus of FIG. 1;

FIG. 4 is a rear view of the X-ray apparatus of FIG. 1;

FIG. 8 is a front, end view of the X-ray apparatus in the transporting mode of FIG. 5;

FIG. 9 is an enlarged, partially cross-sectional view of the carriage drive system for moving the X-ray unit vertically;

FIG. 9A is a plan, partial view of the carriage in vertical lifting system for the X-ray unit shown in FIG. 9;

FIG. 10 is a side, elevational view partially sectioned of the apparatus in FIG. 9;

FIG. 11 is a front view of the electronic rack;

FIG. 12 is a side view of the electronic rack.

DETAILED DESCRIPTION OF THE PREFERRED EMBODIMENT

Figure 6:
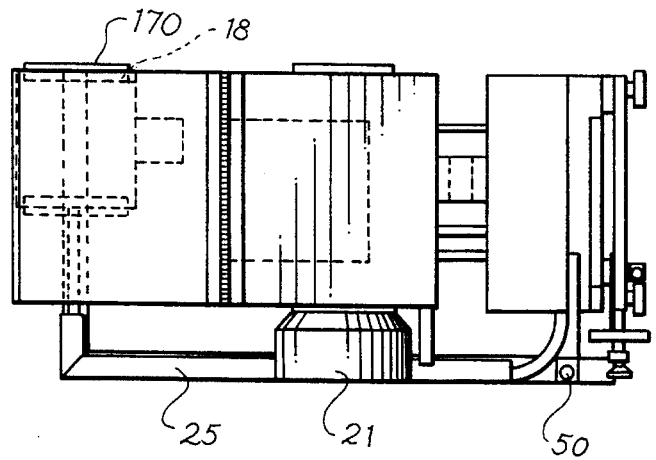
FIG. 6 is a plan view of the X-ray apparatus shown in FIG. 5 in the transporting mode.

As shown in the drawings for purposes of illustration, the invention is incorporated in a portable X-ray 10 which is best shown in FIG. 1 comprises a wheeled cart 11 having a plurality of front wheels 12 and rear wheels 13 which allow the cart to be pushed along a given surface 14 in the transport mode. On the particular cart is carried an X-ray unit 16 which includes a first X-ray unit or X-ray generator 18 for generating a collimated X-ray beam for travelling along a path 19 to another portion of the X-ray unit such as an image intensifier 21. The patient in this preferred embodiment of the invention, is seated in a wheelchair in a space 23, as shown in FIG. 3, between the X-ray generator 18 and the image intensifier 21, with the X-rays passing through the swallowing area in the throat of the person so that a real time or fluoroscopy of obtained of the patient's throat and the person's muscles and tissue during swallowing. Manifestly, the size and the height of the patients will vary considerably and the X-ray unit 16 can be moved vertically from a lower solid line position, shown in FIG. 1, upwardly approximately 25" to an upper position, as shown in dotted lines in FIG. 1. The image intensifier and the X-ray generator including its C-arm 25 are both mounted on a vertically movable carriage 28 which is vertically movable along an upright column 29 means on the cart. In addition to the aforementioned X-ray unit 16 and the C-arm, the apparatus also includes a video monitor 30 which allows the operator to view the moving X-ray images as they are being formed; and there is also an electronic rack 32 which includes a first VCR 33, a second VCR 34, a computer module 35 and an image enhancement electronics module 36.

The X-ray cart is designed to have a working condition or mode, as illustrated in FIGS. 1–4, where the C-arm 25 is swung out, the video monitor 30 is raised, and the X-ray generator is raised. The X-ray cart also has a transporting condition or mode, as illustrated in FIGS. 5–8, in which the C-arm is swung inwardly, the video monitor lowered, and the X-ray generator stowed within the cart confines or volume for transport. In the transporting condition, the X-ray cart should be readily positioned or moved through doors which have a standard width, often only 27" in width, and into the usual elevator in a nursing home or the like which will have a depth of only 57". While it is possible to transport the apparatus on a specialized truck or van, the illustrated volume is only 47.5" in height from the bottom of the wheels to the top of the unit in its transport mode, which height has been found to be easily positioned within a conventional van, which can then be used to transport the apparatus. The illustrated apparatus has a particular given weight of over 400 lbs. including the cart, and the apparatus needs particularly good wheels and a smooth, rolling function to roll over soft carpets inside a nursing home, as well as over paved parking lots. Also, another problem to be solved is that the 400 lb. cart with the X-ray apparatus should not be allowed to ever run away, and it is preferred to provide an automatic braking system therefor.

In accordance with the present invention, there is provided a new and improved portable X-ray apparatus which has a folded C-arm 25 which is held in a very stable, rigid position at a location outwardly of the cart frame, as shown in FIG. 3, at a distance, i.e., almost four feet from the cart frame, by a stabilizing means 38 which in this instance is in the form of a stabilizing arm 40. The stabilizing arm 40 is swung from an upper stowed, transport position as shown in FIGS. 5–8, into the working position, as shown in FIGS. 2 and 3. Specifically the stabilizing arm 40 is pivotally mounted at a lower end on a pivot pin 42 and has at its outer end a stabilizing pad or foot 44 which, when swung downwardly to abut the ground (as shown in FIG. 2) serves to provide additional stability at a position considerably outwardly from the cart frame, as shown in FIG. 3. The preferred stabilizing pad includes a screw-threaded foot member 45 which has a screw 46 which can be turned inside a threaded nut 47 on the arm to adjust the pad height relative to the floor 14 to compensate for unevenness of the floor.

Figure 5:
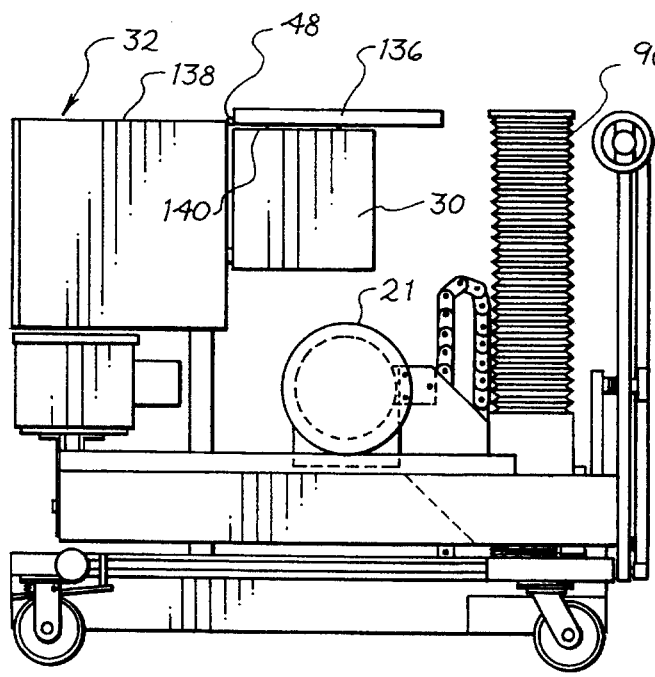
FIG. 5 is a side, elevational view of the X-ray apparatus of FIG. 1 with the apparatus folded inwardly into the transporting mode or condition.

In accordance with another important aspect of the invention, the height limitation is obtained, e.g., 47.5", for the transporting mode by swinging the video monitor 30 from its upright working position is shown in FIGS. 1 and 2 about a pivot means downwardly to a stowed position above the image intensifier 21 (as shown in FIG. 5). To also stow the X-ray generator 18, and the C-arm 25 within the 27" limitation (see FIG. 8), the C-arm is swung about a vertical, pivot axis 50 into a space 51 (FIG. 2) located beneath the electronic rack 32, as shown in FIGS. 5–8.

Figure 7:
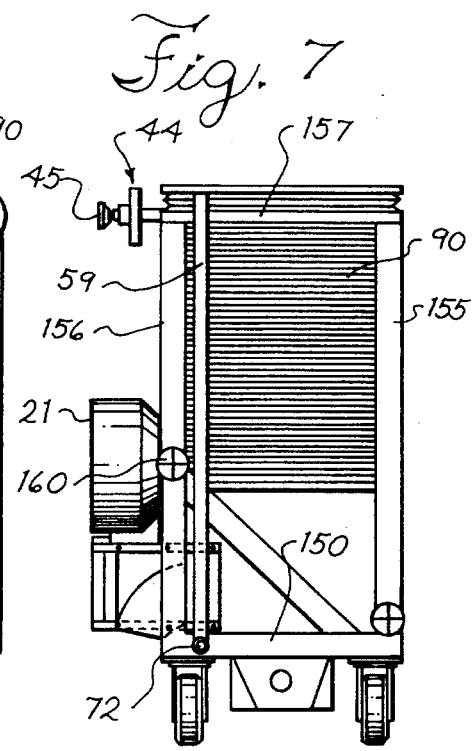
FIG. 7 is a rear end view of the X-ray apparatus shown in FIG. 5 in the transporting mode.

In accordance with still a further aspect of the invention, the X-ray cart is self-braking and includes a brake means 54 located at the front wheels 52 which is urged as by a spring means 55 into engagement to brake the wheels against movement of the cart, as when taking a video X-ray, or whenever a brake actuator 58 is not manually held in not a brake or release position shown in FIG. 4. The preferred actuator 58 is a long lever or rod 59 which must be swung and held in the vertical position, as shown in FIG. 7, against a spring bias force which tends to rotate the actuating rod 58 to an inclined position, as best seen in FIG. 4, and to rotate the brake means to brake the front wheels against rotation.

Referring now to the present invention in greater detail, FIG. 8 shows the maximum width of the volume which, in this instance, is preferably about 27" and in FIG. 5 shows the height dimension in the transport mode, which in this instance is 47½" in height. The length or depth in which the device will be positioned within an elevator is 56".

The preferred and illustrated C-arm, as shown in FIG. 1, is an aluminum, hollow, tubular channel 67 having an inner end pivotally mounted between a pair of upper and lower plates 61 and 62 (FIG. 9) with a vertical axle or pivot pin 63 mounted between the plates 61 and 62. The pivot pin 63 is mounted in a bronze bearing 64 (FIG. 9) positioned between the plates 61 and 62 and the pivot pin and bearing are lapped to eliminate play therebetween so that the X-ray generator 18 will be precisely aligned so that the beam will be on the centerline of the image intensifier when the C-arm is swung to its outward position as shown in FIGS. 1 and 3. Play in the bearing would, of course, adversely affect that particular alignment. It is to be understood that the particular image area on the image intensifier is kept within very careful precise amounts, for example, a 2% variance in area with a fixed focal length. The beam generator generates an X-ray that has a circular area of approximately 9" in diameter in this instance.

The preferred and illustrated use of the image intensifier 21 is to take fluoroscopic images without any still images of the patient seated in a wheelchair in the space 23 while the patient is swallowing so that the swallowing muscles, tissues, etc. can be viewed and recorded. There is provided on the X-ray generator a masking device or means 70 (FIG. 1) which has a preferred construction shown in a co-pending application filed of even date, entitled "X-ray Mask and Apparatus". The masking unit blocks "bloom" from interfering with the contrast as fully described in the co-pending application, which application is incorporated by reference as if fully reproduced herein.

The C-arm 25 includes the long arm portion 25a that is attached at one end to the pivot pin 63 and that has at its outer end a right angle portion 25b (FIG. 3). The right angle portion 25b carries a pair of upstanding brackets to which the generator 18 is bolted.

The hollow interior of channel of the C-arm 25 also serves as an electrical conduit holder through which the conduits lead from the X-ray generator 18 through the length of the C-arm to adjacent the pivot pin 63 at which the electrical conduits pass into a horizontal duct 67 under the frame of the cart. The cart frame includes a pair of tubular members 68 and 69, (FIG. 9) which, in this instance are steel, instead of aluminum, to give additional strength to the cart frame. The cart frame is formed with two cross frame channels 71 and 72 welded at the forward and rearward ends of frame tubular members 68 and 69. The cross channel 72, as best seen in FIGS. 9 and 10, is a 2"×10" tube that is welded to the rear ends of the steel tubular frame members 68 and 69. At the front of the cart, a 2"×6" cross tubular channel 71 is welded to the front end of tubular members 68 and 69.

Electric cables extend down through a hollow vertical post or channel 74 (FIG. 2) on which is mounted the vertically disposed rack 32 containing the electronic components. As can be understood, there will be a lot of wire connections from the computer, video recorders and the image enhancer, electronic units down through the post 74 and into the horizontal duct 67 and then over to the image intensifier unit 21, and to and from the latter into a conventional cable carrier 76. The cable carrier 76 has one leg 76b extending down to the duct 67 under the floor of the cart, with the other leg 76a extending to the image intensifier 21. As the carriage 28 moves vertically, the U-shape changes in the number of lengths in each one of the depending legs 76a and 76b as the cables therein move between the legs as the carriage travels relative to the cart frame.

Referring now in greater detail to FIGS. 9, 9A and 10, the internal construction of the column means 29 and the carriage 28 will now be described. The column means 29 includes a formed, vertical, column or post 29a which is vertically mounted and secured at its lower end by brackets to the horizontal, frame, cross-channel 72 of the cart. A second parallel vertical column or post 29b is spaced from and parallel to the vertical column 29a. The carriage includes a central carriage frame 84 (FIG. 10) which includes a vertical plate 85 and an upper, horizontal plate 86 to which is attached a lead screw nut 87 through which passes a vertical lead screw 88. The upper end of the lead screw is journaled in a bearing which is carried by a stationary horizontal cross bar 89 which is attached at its opposite ends to the top ends of the vertical columns 29a and 29b, as best seen in FIG. 9. The cross bar 89 also supports an upper end wall of a bellows 90 which covers the columns and the lead screw to avoid places where the elderly or an operator may come in contact with and be pinched by moving pieces of the carriage or the turning of the lead screw.

The carriage 28 supporting the X-ray generator and the image intensifier is driven by a motor 92 (FIG. 10) which drives a suitable gear box 93 having an output shaft vertically aligned with the lead screw and a clutch mechanism 94, which is provided to clutch the lead screw to the motor drive when it is desired to turn the lead screw in the lead nut 87 to raise or lower the X-ray unit relative to the patient who is typically sitting in the wheelchair.

To prevent a patient from contacting the lower end of the lead screw 88 or the clutch mechanism 94, there is a second, small, round or cylindrical bellows 96 which is attached at its upper end to a lower horizontal plate 98 which is affixed to the vertical frame plate 85. The lower end of the bellows is attached to the stationary rear channel 72, which is part of the cart frame and is welded to the two steel, tubular frame 68 and 69 (FIG. 9). The latter extend the length of the cart and form with the channels 71 and 72 the main frame of the cart. The motor 92 and the gear box 93 are disposed within the interior of the cable duct 67, which is at the bottom part and below the steel frame members 68 and 69, as shown in FIG. 9. The duct 67 not only covers the motor but also serves as an internal duct in which are the cables and wires which extend to the various electrical equipment such as the X-ray generator on the C-arm.

The preferred column means 29 is comprised of two different vertical columns 29a and 29b with the main support and more expensive, vertical column 29a being a tube-like channel which is a 2"×3" tubing and is quite strong with a ¼" sidewall. The vertical column means 29 includes a vertical, stationary slide bar 81 of cruciform shape with smooth slides on which slides a first, upper main bearing slide 110 (FIGS. 9 and 9A) which is mounted on the main support plate 112. A similar lower slide 114 is also attached to the main plate 112 and slides along the vertical slide bar 81 as the carriage travels along the stationary column 29a. On the other vertical stationary column 29b is a vertical, stationary slide bar 83 which has an angle iron shape and is less expensive than the slide bar 81. The carriage has rollers 120 which roll along opposite vertical sides of the flange leg 83a of the slide bar 83. The carriage 28 comprises a central, vertical extending intensifier support plate 103 which is abutted at right angles to and is secured at its inner end 103a to the vertically extending plate 112. The plate 112 has brackets 119 that carry the rollers 120 that roll vertically along opposite sides of flange leg 83a of the angle-shaped bar 83. Another flange leg 83b of the angle-shaped bar 83 is secured to the side of the stationary post 29b. The upper and lower slide bearings 110 and 114 are mounted to the vertical carriage plate 112 and have portions interfitted into the dovetail shaped, cross-sectional shape of the vertical slide bar 81, as best seen in FIG. 9A. The vertical slide bar 81 is fastened to one side of the stationary, vertical post 29a.

Turning now in greater detail to the automatic braking system, which automatically brakes the wheels 12 to prevent the cart from being a runaway, the brake actuator 58 is preferably a form of a long, vertical extending rod which, as shown in FIG. 4, is about almost at a 30° angle with respect to the vertical. The rod is relatively heavy and it is secured at its lower end to one end of a horizontal shaft 72 which is journaled for turning in the cart frame by its bearing 125 (FIG. 4) at the end adjacent the handle, and which is journaled in a bearing at its opposite end for turning in a bearing in the front channel 71. The shaft 72 extends from the rear end of the cart along the floor of the cart to the front wheels 12 at which the shaft 72 carries an actuating mechanism or eccentric cam 128 (FIG. 2). The cam has a lower side which bears against an end 130 of a pivotally mounted braking plate 132. The braking plate 132 is pivoted at a pivot pin 134 on the frame with the forward end 136 of the braking plate 132 being adapted to engage the front wheels 12 at the top front portions thereof to apply a braking force thereto. Between the front end 136 of the braking lever 132 and the overhead channel 71 are mounted the pair of compressed springs 55 which, in this example, are each applying a force of about 100 lbs. to pivot the braking plate 132 into engagement with the wheels 12. A large mechanical advantage is provided at the upper end of the lever actuator 58 so that only a force of about 20–30 lbs. is necessary to be supplied by the operator to pivot the lever actuator 58 counterclockwise (as viewed in FIG. 4) to the release position, as shown in FIG. 7 wherein the actuator rod 58 is vertical. When the actuator rod is in this vertical position, the cam has pivoted the braking plate in a clockwise direction to release the frictional braking engagement and the cam holds the braking plate against pivoting toward the wheels from the 200 lb. biasing force of the springs 55. When the operator for any reason releases the 20 lbs. or force holding the actuator lever 58 in the vertical position, the force of the 200 lbs. of spring force from the springs 55 pivot the braking plate 132 toward the wheels and to pivot the actuator lever 58 to the position shown in FIG. 4 to brake the wheels against further rolling movement.

The video monitor 30 is mounted in its stowed position, as shown in FIG. 5, wherein it is located above the image intensifier 21 and is within the height and below dimension of 47.5". In use, the video monitor is swung about the piano hinge 48 to the upper position shown in FIGS. 1 and 2 in which the video monitor extends considerably above the 47.5" limit for transport. Herein the video monitor 30 is mounted on a turntable 132 which includes a lower plate 134 fixed to a pivoted base plate 136. The base plate 136 is connected at one end to the piano hinge with the other end of the piano hinge being fastened to upper wall 138 of the electronics rack 32. The turntable includes a rotatably plate 140 which is fastened to the video monitor's underside and which rotates on bearings within the plate 134. When the video monitor 30 is positioned in the upper working position, as shown in FIGS. 1 and 2, the video monitor may be rotated about the vertical axis through the turntable to any position to assist the operator in viewing the X-ray images as they are being taken.

It will be recalled that the stabilizing arm 40 generally took the position shown in FIGS. 2 and 3 and 4 when the X-ray unit was in the operating position with the stabilizing arm being rotated down into a generally horizontal position. As shown best in FIGS. 3 and 4, there is a threaded screw 150 having an enlarged knob 151 which threads through the arm into a threaded hole 153 in a vertical support member for the cart frame. This screw keeps the stabilizing arm locked and rigid with the cart and serves to transfer forces between the cart and the stabilizing arm. The C-arm 25 is held against pivoting when the arm is swung out to its working condition of FIG. 3 by another screw 150a having a knob 151a for extending through a hole in a portion of the arm 25, and being threaded into a thread hole in the cart frame. By turning the knob and removing the screw, the arm may be swung inward to its stowed, transport position.

The preferred stabilizing arm includes a pair of parallel support members 155 and 156 (FIG. 4) which are joined at their outer ends by a handle bar 157 which extends across and is fastened at its opposite ends to the outer ends of the support members 155 and 156. When in the vertical position, as best seen in FIG. 7, the handle bar 157 will be generally horizontally disposed and the members 155 and 156 will be vertically disposed. The foot 144 serves no useful function when the stabilizing arm is swung upwardly about the pivot point into its cart pushing position. Opposite from the handle bar is a second cross member 158 which joins the other ends of the members 155 and 156 to form a generally rectangular structure for the stabilizing arm and handle. In the stowed position, a threaded lock knob 160 is inserted through an opening in the now vertical member 156, as best seen in FIG. 7, and is threaded into the opening 153 in the vertical frame member 154 of the cart to lock and hold rigid the stabilizing arm with the cart frame, now in its upper handle operating position, as shown in the transporting position of FIGS. 5 and 7.

As best seen in FIGS. 11 and 12, the electronic rack 32 has an outer, sheet metal cover 160 to which are attached C-shaped shelves 161a–161d, each having two edges for supporting edge portions of an electronic module 33–36 slid thereacross. Each electronic module spans a pair of shelf edges in the same horizontal plane. To clamp the electronic modules against theft from the rack, each module will be clamped down from above by an appropriate lock bar 163a–163d against its associated lower pair of shelf edges which are supporting the opposite edges of the electronic modules. The electronic modules are generally rectangular and are slid horizontally into the shelf racks with the cover protecting the rear and vertical sides of the electronic modules.

The lock bars 163a–163d extend horizontally across the top of electronic modules (33–36) and are pulled down thereagainst by turning of pairs of associated screw rods 172 in their respective nuts 167a–167d fastened to a lower plate 169 of the electronic rack. The screw rods each have a head 171a–171d accessible from below. Turning of a pair of screw heads in their associated nuts 172 for a given lock bar moves the given lock bar vertically. For example, turning of the screw heads 171d of the shortest screw rods 165d may pull the locking bar 163d tightly down against the top of the module resting on shelf edges 161d to clamp the module against lower plate 169. There are four different heights for the four different screw rods, as shown in FIG. 12. Thus, the electronic modules may be clamped in a simple and inexpensive manner without raising the height of the electronic rack.

From the foregoing, it will be seen that in the transporting condition shown in FIG. 5, 6, 7 and 8, that the video monitor 30 is swung downwardly to be below the vertical height limitation e.g., 47.5" and that the top plate of the bellows unit 88 is also at this location; whereas, in the operating condition, the video monitor is swung upwardly and the bellows may extend upwardly of the 47.5" height limitation. Also, as shown in FIGS. 6 and 8, the video generator 18 and the C-arm 25 are swung inwardly into the confines of the cart so that the total width of the cart is less than 27" in width, as viewed in FIG. 7. From a depth standpoint, the entire video cart (as seen in FIG. 5) from the handle portion to the front side 165 of the tray 32 is within the desired dimension of 56" so that the cart may be positioned within an elevator having a 57" depth. As best seen in FIG. 8, the maximum width between the front face 168 of the image intensifier 21 and the side of the X-ray generator 18 is less than 27".

The apparatus is quite rugged in that most of the parts are made of tubing and are fairly simple mechanical constructions which may be used over and over again with relatively little maintenance and which can be made at a low cost. Also, the unit is made to be very stable and rigid in its operation particularly for stabilizing the C-arm with the use of the stabilizing arm 40. The unit is very simple to set up merely by unscrewing some of the screw knobs and swinging the stabilizing arm 40 from its transporting vertical position to its generally horizontal stabilizing position. A screw knob is then used to secure the stabilizing arm to the frame. When the X-ray unit is being used, the brake actuator lever 58 will be in the operating, inclined position shown in FIG. 4 with the wheels being braked so that the unit remains stable and does not move during the taking of the X-rays. The particular arrangement allows a wheelchaired person to be wheeled into the position between the image intensifier 21 and the X-ray generator 18 with the height of the X-ray generator 18 and the image intensifier 21 being adjusted vertically between the positions shown in FIG. 1 to align the path of the beam through the throat of the patient taking fluoroscopic X-rays of the person as they are swallowing. The video tape recorders 33 and 34 will take video images during the patient's neck during swallowing. The entire operation is adapted to also take still images, if so desired; but herein, the preferred use is to have fluoroscopy with video tape recording of the movements of the patient swallowing mechanisms.

An important aspect of the invention is that the X-ray apparatus is essentially a one-piece piece apparatus that does not have to be assembled from separate pieces in order to use same and disassembled into multiple pieces for transport. For example, the C-arm is not two pieces that have to be assembled and disassembled in the nursing home for separate transport of the C-arm pieces. Also, all of the X-ray electronic controls and wiring are preassembled and attached to X-ray generator, the image intensifier and the electronics on the wheel apparatus so that there is no separate electronic control package that must be connected to X-ray units at a nursing home location and then disconnected for transport.

What is claimed is:

1. A portable X-ray apparatus suitable for wheeling into elevators, through doors, and into vehicles, said apparatus comprising:

a cart having wheels for rolling through doors, and into elevators;

an x-ray means including an x-ray generator unit and an x-ray image intensifier unit carried on said cart;

a support arm pivotally mounted on said cart for carrying one of said x-ray units from a stowed transport position on said cart to an outboard operative position outward of said cart for x-raying a patient;

the other of said x-ray units being mounted on the cart in alignment with the first x-ray unit;

a vertically movable carriage on said cart supporting said image intensifier unit and said generator unit to provide verticle movement thereof to obtain vertical alignment with a patient; and a stabilizing arm movable from a stowed first position on said cart to an outer position to stabilize said support arm and said cart against tipping.

2. An x-ray apparatus in accordance with claim 1 further including an automatic braking means for braking said wheels to keep said cart from rolling movement unless said breaking means is being disabled by an operator when pushing said cart.

3. An x-ray apparatus in accordance with claim 2 wherein said stabilizing arm has a handle portion movable to a position to act as a push handle when the stabilizing arm is in its stowed transport position, and a brake release actuator positioned adjacent said handle and holdable to release said brakes against any biasing force which urges said brake means to brake said wheels.

4. An x-ray apparatus in accordance with claim 1 further including a video monitor mountable on said cart, said monitor being pivotable between a stowed carrying position to an operative position for viewing of an x-ray operation.

5. An x-ray apparatus in accordance with claim 1 further including a vertical guide mounted on said cart, said carriage traveling vertically along said vertical guide, and a vertically expandable bellows covering said vertical guide and portions of said carriage to prevent touching of said carriage and said guide by operators involved in taking of the x-rays.

6. An x-ray apparatus in accordance with claim 1 further including vertical supports for said carriage mounted on the cart and having a predetermined height and said carriage traveling to a height above the predetermined height.

7. A manually movable x-ray apparatus comprising:

a cart having wheels to enable pushing of said cart through doors and into elevators and onto vehicles for transport to patients;

an x-ray means on said cart including an x-ray generator unit and an x-ray image intensifier unit;

said apparatus having a predetermined transport volume defined by a predetermined height, width and depth allowing said cart to pass through doors and to fit into elevators;

a pivotally mounted support arm on said cart carrying one of said x-ray units on an end thereof and positioning said one x-ray unit within said transport volume when the arm is in a stowed transport position, said arm being mounted on said cart for swinging said one x-ray unit several feet outside of the transport volume when said arm is in an operative position outside of said transport volume;

a video monitor unit on the cart movable from a stowed carrying position on the cart within the transport volume to an operative position outside of the transport volume; and a stabilizing means for said cart and operative when said support arm and said one x-ray unit are swung outwardly of the transport volume into said operative position, said stabilizing means movable from an inward stowed first position within the transport volume to an outer operative position outside of the transport volume.

8. An apparatus in accordance with claim 7 wherein said stabilizing means comprises a pivotally mounted arm and a pad at a distal end of the arm to engage the floor at a point located outwardly of the transport volume.

9. An apparatus in accordance with claim 8 wherein an automatic breaking means is mounted on said cart to brake said wheels, spring means on said brake means for biasing said brake means to engage said wheels to stop rolling movement of said cart; and a manual actuator mounted on said cart and held by a cart operator to release said brakes for movement of said cart.

\* \* \* \* \*